US006984361B2

(12) United States Patent
Carman et al.

(10) Patent No.: US 6,984,361 B2
(45) Date of Patent: *Jan. 10, 2006

(54) USE OF CONTINUOUS FLOW OF $O_x$ TO CONTROL BIOLOGICAL PATHOGENS IN MAIL AND SHIPPING PARCELS

(75) Inventors: Gary B. Carman, Reno, NV (US); Stephen K. Wirtz, Sparks, NV (US)

(73) Assignee: Cosmed Group, Inc., Jamestown, RI (US)

( * ) Notice: Subject to any disclaimer, the term of this patent is extended or adjusted under 35 U.S.C. 154(b) by 553 days.

This patent is subject to a terminal disclaimer.

(21) Appl. No.: 10/041,660

(22) Filed: Jan. 10, 2002

(65) Prior Publication Data

US 2002/0150500 A1    Oct. 17, 2002

Related U.S. Application Data

(63) Continuation-in-part of application No. 09/903,685, filed on Jul. 13, 2001, now Pat. No. 6,793,884, which is a continuation of application No. 09/217,581, filed on Dec. 22, 1998, now Pat. No. 6,284,193.

(60) Provisional application No. 60/068,668, filed on Dec. 23, 1997.

(51) Int. Cl.
*A61L 9/00*    (2006.01)

(52) U.S. Cl. .......................... 422/33; 422/22; 422/23; 422/28; 422/30; 422/186.07

(58) Field of Classification Search ................. 422/33, 422/22, 23, 28, 30, 186.07, 292
See application file for complete search history.

(56) References Cited

U.S. PATENT DOCUMENTS

| 5,302,358 | A | 4/1994 | Andersen et al. |
| 5,749,203 | A | 5/1998 | McGowan, Jr. |
| 5,783,242 | A | 7/1998 | Teague |
| 5,833,740 | A | 11/1998 | Brais |
| 6,228,330 | B1 | 5/2001 | Herrmann et al. |
| 6,284,193 | B1 * | 9/2001 | Carman et al. ............... 422/33 |

OTHER PUBLICATIONS

Kelly-Wintenberg et al., "Room temperature sterilization of surfaces and fabrics with a One Atmosphere Uniform Glow Discharge Plasma", Journal of Industrial Microbiology & Biotechnology, 20, pp 69-74, (1998).

Schutze et al., "The Atmospheric-Pressure Plasma Jet: A Review and Comparison To Other Plasma Sources", IEEE Transactions On Plasma Science, vol. 36, No. 6, Dec. 1998.

Herrmann et al., "Decontamination of chemical and biological warfare (CBW) agents using an atmospheric pressure plasma jet (APPJ)", Phys. Plasmas, vol. 6, No. 5, May 1999.

* cited by examiner

Primary Examiner—Krisanne Jastrzab
(74) Attorney, Agent, or Firm—Patton Boggs LLP

(57) ABSTRACT

A gaseous blend of Ox and a method for significantly reducing the biological load, including anthrax, on mail and shipping parcels is disclosed. The gaseous blend of Ox consists at least in part of $O_3$. The method involves applying a continuous stream of oxygen-containing, i.e., Ox, gas to the mail or shipping parcel at a predetermined temperature, pressure and relative humidity. The continuous stream of Ox gas is prepared in an Ox generation cell, which contains a means for generating the Ox gas at a pressure less than 20 lbs/in2 using, for example, one or more of the following: corona discharge, high frequency electrical discharge, ultraviolet light, x-ray, radioactive isotope and electric beam.

11 Claims, 3 Drawing Sheets

USE OF CONTINUOUS FLOW OF $O_X$ TO CONTROL BIOLOGICAL PATHOGENS IN MAIL AND SHIPPING PARCELS

The application is a Continuation-in-part of U.S. application Ser. No. 09/903,685, filed Jul. 13, 2001 (now U.S. Pat. No. 6,793,884), which is a Continuation of U.S. application Ser. No. 09/217,581, filed Dec. 22, 1998 (now U.S. Pat. No. 6,284,193), which is a regular national application claiming priority from provisional Application Ser. No. 60/068,668, filed Dec. 23, 1997 (abandoned). U.S. application Ser. No. 09/689,631, filed Oct. 13, 2000 (now U.S. Pat. No. 6,334,979); and U.S. application Ser. No. 60/276,041, filed Mar. 16, 2001 are related to this application. The entirety of each application is incorporated herein by reference.

BACKGROUND OF THE INVENTION

1. Field of the Invention

The present invention generally relates to a gaseous blend of Ox and a method for applying the gaseous blend of Ox to mail components to significantly reduce any detrimental biological pathogens thereon.

2. Background of the Technology

The microbiological security of mail components and in-transit parcels has become a primary concern for both government based mail systems as well as private business. With biological warfare issues on the rise and the potential for accidental contamination with a number of aggressive organisms such as *Bacillus anthracis* (anthrax), hemmoraghic *E. coli*, and numerous virus particles, a system for the sanitization of these suspect parcels is a high priority for the safety of the general population. To date, several systems have been utilized or proposed as control systems. These include cobalt irradiation, electron beam irradiation, high pressure steam, and high intensity ultraviolet (UV).

U.S. Pat. No. 4,151,419 discloses an apparatus for irradiating solids embodying pathogens that includes an irradiation chamber surrounded by a barrier of concrete; an endless conveyor; and an irradiation source, wherein said endless conveyor carries individual open top containers through said chamber.

U.S. Pat. No. 5,833,740 discloses a chemical and biological air purifier that includes a housing having an inlet and an outlet both aligned on a longitudinal axis, a turbulence generator, one or more vacuum ultraviolet (UV) sources to achieve chemical purification and one or more germicidal ultraviolet (UV) sources to achieve biological purification.

U.S. Pat. No. 6,280,601 discloses a method for sterilizing microorganims, including anthrax, that includes applying to at least a pair of electrodes extending into said area to be treated a voltage of at least 0.4 V per meter of electrode distance per pair of electrodes; passing a direct current through said area to be treated to alter the capacitance of the material being treated; and causing an electric discharge therethrough when its capacitance is overloaded.

U.S. Pat. No. 6,228,330 discloses an atmospheric-pressure plasma decontamination/sterilization chamber. The patent discloses that the apparatus is useful for decontaminating sensitive equipment and materials, such as electronics, optics and national treasures, which have been contaminated with chemical and/or biological warfare agents, such as anthrax, mustard blistering agent, VX nerve gas, and the like. Items to be decontaminated or sterilized are supported inside the chamber. Reactive gases containing atomic and metastable oxygen species are generated by an atmospheric-pressure plasma discharge in a $He/O_2$ mixture and directed into the region of these items resulting in chemical reaction between the reactive species and organic substances. This reaction typically kills and/or neutralizes the contamination without damaging most equipment and materials. The plasma gases are recirculated through a closed-loop system to minimize the loss of helium and the possibility of escape of aerosolized harmful substances.

These systems have a number of major constraints to be considered effective on a widespread scale. For example, the irradiation systems are extremely expensive to construct as well as maintain. Such systems are also limited as to the types of parcels that can be treated since they interact with any metal (i.e., staples, paper clips, etc.), which can cause combustion of the parcel. Severe damage to computer disks, photographs as well as magnetic media would require that mail containing these items be sorted out, thus making radiation based processes less than desirable. High pressure steam and any system which involves liquid water or solutions create a plethora of problems with adhesives and printing media. UV systems are only effective as a surface treatment and destroy most common marking systems and inks. In addition, there is a concern in the medical industry that many of these systems will interact with pharmaceuticals and medical devices that are often sent through the mail.

A number of commercial sterilants and fumigants are presently used to reduce biological pathogens. The most widely used are ethylene oxide, hydrogen phosphide, and hydrogen cyanide. As disclosed in U.S. application Ser. No. 09/217,581, many of these compounds pose hazardous conditions for application personnel and can form deleterious residues on the materials that are treated. Furthermore, some of the traditional sterilants and fumigants have been identified with the formation of carcinogens and mutagens.

Ozone ($O_3$) and its primary active component, atomic oxygen, have been used in water and commodity sterilization for about 100 years. However, as discussed in more detail below, prior treatment methods using $O_3$ would be ineffective for treating mail components.

U.S. application Ser. No. 09/217,581 discloses a method and apparatus that uses a gaseous mixture of oxygen-containing gases, i.e., $O_3$, $O_2$ and $O_1$, hereinafter referred to as Ox, to reduce biological loads on consumer products to eliminate pathogens.

U.S. applications Ser. Nos. 09/689,631; 60/276,041; and 09/903,605 disclose additional embodiments of the invention disclosed in application Ser. No. 09/217,581.

SUMMARY OF THE INVENTION

It is desirable to treat mail and shipping parcels in a safe, cost effective manner. The gaseous blend of Ox and method of the present invention permit reduction of biological pathogens (hereinafter referred to as "biological burden reduction") of mail and shipping parcels.

The gaseous blend of the present invention consists at least in part of $O_3$.

The method of the present invention utilizes the gaseous blend of Ox in a technologically advanced treatment system that overcomes the limitations formerly encountered with $O_3$ treatment on biological burden. Prior $O_3$ treatments include, for example, (1) the submersion of an article to be treated in ozone-containing water and the bubbling of ozonated water over the article (see, e.g., U.S. Pat. No. 4,517,159 to Karlson and U.S. Pat. No. 4,640,872 to Burleson); and (2) the static treatment of medical devices and food products with gaseous ozone (see, e.g., U.S. Pat. No. 3,179,017 to Shapiro et al., U.S. Pat. No. 5,069,880 to Karlson, and U.S. Pat. No. 5,120,512 to Masuda). Systems such as those described above have encountered several limitations. The incorporation of ozone gas into water and then submersion of items(s) to be sterilized or the spraying of ozone treated water onto the surface of item(s) to be sterilized limit the process to materials that can be soaked in water. The few gaseous uses of ozone have been limited to the surface treatment of medical devices and the like due to the lack of adequate penetration into materials. Thus, although these past processes have proven the efficacy of ozone as a sterilant and as a fumigant, they are not applicable to the treatment of mail and shipping parcels.

In addition to the generation of the ozone molecule, the present invention also utilizes the quenching effect of other inert gases to assist ozone generation, thereby increasing the stability of the Ox radicals.

Accordingly, it is an object of the present invention to provide a gaseous blend of Ox and a method for applying the gaseous blend of Ox for reducing biological burden from mail and shipping parcels.

It is another object of the present invention to provide a gaseous blend of Ox and method for applying the gaseous blend of Ox for reducing biological burden from mail and shipping parcels in a safe manner.

It is thus an object of the present invention to eliminate the health risks that are associated with the reduction of biological burden.

It is a further object of the present invention to provide a simple, efficient and economical gaseous blend of Ox and a method for applying the gaseous blend of Ox for reducing biological burden from mail and shipping parcels that can be used at the site of mail pick up as well as at mail processing facilities.

In accordance with the above and other objects, the inventive gaseous blend consists of at least $O_3$. The inventive method for applying the gaseous blend comprises applying a continuous stream of Ox gas to the mail or shipping parcel.

The continuous stream of Ox gas is prepared in an Ox generation cell, which contains a means for generating the Ox gas at a pressure less than about 20 lbs/in$^2$, for example, one or more of the following: corona discharge, high frequency electrical discharge, ultraviolet light, x-ray, radioactive isotope and electron beam.

As discussed herein, $N_2$ and/or $CO_2$ may be added during Ox treatment. The addition of 0%–70% $N_2$ and/or 20%–100% $CO_2$ increases the generation of an Ox quenching effect.

An apparatus such as that disclosed in application Ser. No. 09/217,581, may be used to carry out the method of the invention.

The apparatus disclosed in application Ser. No. 09/217,581 comprises:

(a) a biological burden reduction chamber;

(b) a vacuum pump coupled to the biological burden reduction chamber;

(c) an Ox generation cell, wherein the Ox generation cell contains a means for generating Ox at pressure less than about 20 lbs./in2 using, for example, one or more of the following: corona discharge, high frequency electrical discharge, ultraviolet light, x-ray, radioactive isotope and electron beam;

(d) a first control valve coupled to the biological burden reduction chamber and the Ox generation cell, wherein the first control valve is capable of permitting Ox to be drawn from the Ox generation cell into the biological burden reduction chamber; and (e) a second control valve coupled to the biological burden reduction chamber, wherein the second control valve is capable of withdrawing Ox contained within the biological burden reduction chamber out of the biological burden reduction chamber.

Water vapor may be introduced to the gaseous Ox to maintain an appropriate humidity level, i.e., between about 20% and 98% relative humidity, and, more preferably between about 40% and 75% relative humidity. The appropriate humidity level is dependent upon the ambient humidity. Depending on the length of treatment time, any vacuum that may be created during the process removes humidity, thus requiring the addition of humidity. The Ox gas may then be passed through a commercially available catalytic destruct unit to eliminate any residual $O_3$ and $O_1$ before the gas stream is discharged to the atmosphere.

Additional objects and attendant advantages of the present invention will be set forth in the description and examples that follow, or may be learned from using the gaseous blend or practicing the method of the present invention. These and other objects and advantages may be realized and attained by means of the features, instrumentalities and/or combinations particularly described herein. It is also to be understood that the foregoing general description and the following detailed description are only exemplary and explanatory and are not to be viewed as limiting or restricting the invention as claimed.

The invention itself, together with further objects and attendant advantages, will best be understood by reference to the following detailed description, taken in conjunction with the accompanying drawings.

BRIEF DESCRIPTION OF THE DRAWINGS

In the following description, like parts are designated by like reference numerals throughout the figures.

DESCRIPTION OF PREFERRED EMBODIMENTS

Figure 1:
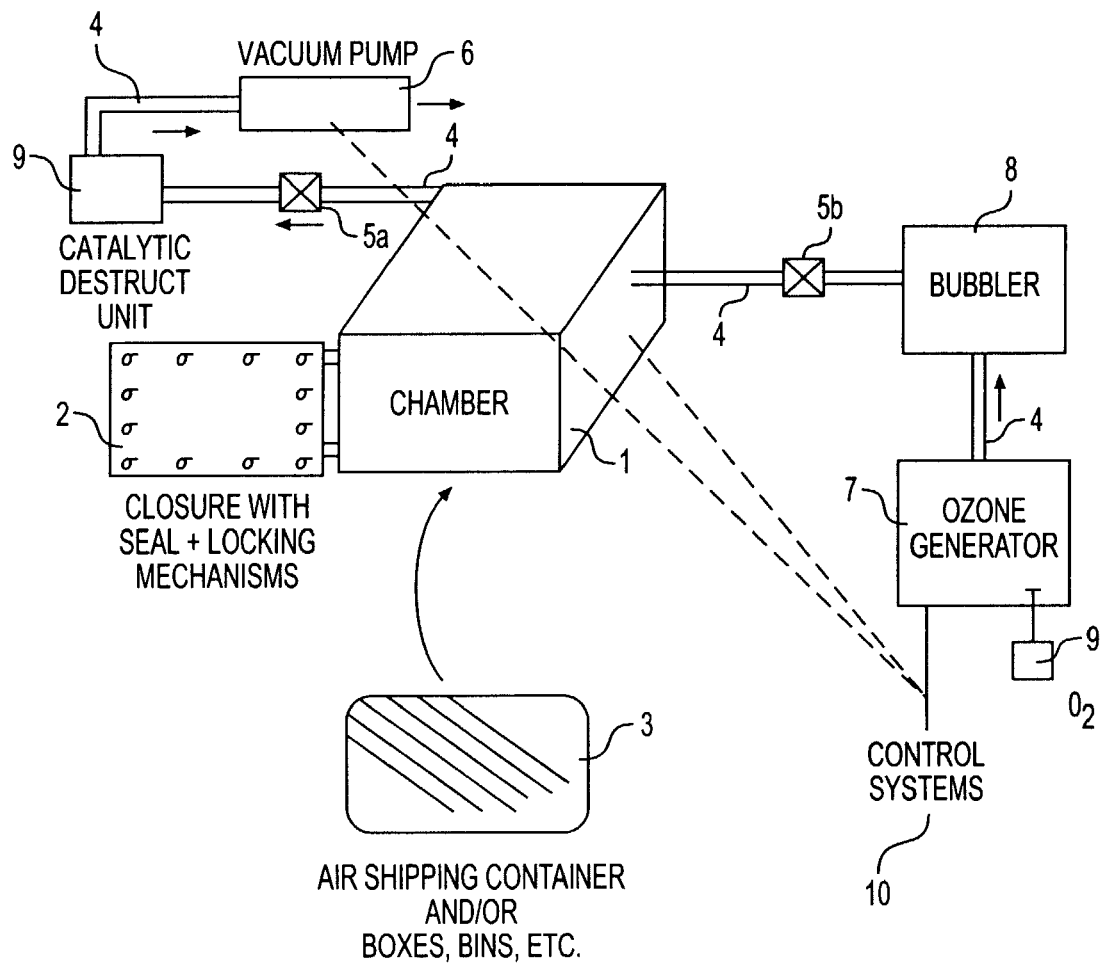
FIG. 1 is a schematic showing one example of an apparatus for using a continuous flow of Ox to reduce biological burden on mail and shipping parcels in accordance with the method of the invention. Such an apparatus can be employed at a mail processing facility.

All patents, patent applications and literatures that may be cited herein are incorporated herein by reference.

The antibacterial potential of $O_3$ has been recognized for many years. $O_3$ is widely used as a disinfectant for sewage treatment and for purification of drinking water. It has, however, failed to gain acceptance as a biological burden reduction treatment. The primary reason for this failure is that the $O_3$ molecule is highly unstable and quickly reverts to $O_2$ if it does not encounter a susceptible substrate with which to react.

Previous attempts to use $O_3$ as a biological burden reduction treatment include the reliance upon filling a sterilization chamber with $O_3$ and exposing the materials to be treated in static fashion for various periods of time without replenishment of $O_3$. See, for example, U.S. Pat. Nos. 3,719,017 and 5,069,880. Under these conditions, the concentration of $O_3$ within the chamber would be expected to rapidly decrease to a level below that required for effective biological burden reduction due to the short half life of $O_3$, which is typically less than 20 minutes. A further disadvantage of the static exposure technology is the reliance on simple diffusion to promote permeation of the $O_3$ molecules through packaging materials and into interstices of the materials being treated. Thus, such methods do not achieve adequate permeation into the material being treated.

DETAILED DESCRIPTION OF THE INVENTION

The present invention is based on the process described in U.S. Pat. No. 6,284,193 B1 which utilizes a continuous flow of an $O_x$ laden gas stream in a vacuum vessel. One of the embodiments of this invention is directed to an apparatus and method that could be employed on-site at the mail processing facility. The apparatus includes a rigid vacuum chamber which can be loaded with a quantity of bulk mail in bins, carts, air shipping containers, boxes, or any gas permeable container and then sealed and processed in accordance with the previously stated process. In this manner, an absolute minimum of personnel contact as well as a complete sterilization of the parcels and the parcel containers are achieved.

Another embodiment is directed to an apparatus and method that can be employed in the field during mail and parcel pickup. The apparatus includes a flexible vacuum chamber that can be manufactured from an ozone resistant polymer constructed of sufficient thickness to withstand the required vacuum and abrasion issues. In addition to a rapid deployment closure system for the polymer chamber, a number of gas inlet and outlet ports are configured so as to allow the flowing gases to evenly penetrate the quantity of mail containers. The temperature of the bag enclosure and its contents is achieved by traditional HVAC systems. A bubbling chamber is utilized to precondition the gas flow as well as supply a low level of humidification to enhance the biocide effectiveness of the gas stream. An advantage of this system is the reduction of open space within the chamber, thereby reducing the quantity of competing gases within the chamber as well as reducing the quantity of $O_x$ gas needed to achieve the required treatment. This system is also a very cost effective way to locate treatment chambers at numerous locations with a minimum investment as well as allowing the portability of the chamber from site to site as demand changes. All control systems, sensors, and hardened machinery are located external to the flexible chamber which aids in the rapid loading and unloading of the chamber.

Each system would typically utilize a normal treatment time of 4 to 20 hours with a typical ozone concentration of about 0.03 to 16%, and more preferably about 4%. The temperature range is between 40° F. and 100° F. with the humidity level being maintained below the dew point of the ambient temperature. Vacuum levels are typically increased to increase the permeation of the mail components. The effective range is between 1 and 20 inches of mercury. The gas mixture typically is composed of a majority of oxygen, but may also include significant percentages of carbon dioxide and/or nitrogen.

The present invention, which has been designated "dynamic Ox biological burden reduction," offers significant advances over the prior static biological burden reduction technology in that it provides a continuous flow of Ox, i.e., between about 0.03% and 16%, throughout the treatment cycle and promotes rapid permeation of Ox through packaging materials and into the voids and interstices of the materials undergoing treatment. Continuous operation of the vacuum pump and Ox generator during biological burden reduction ensures that the concentration of Ox remains essentially the same throughout the process by constantly supplying newly generated Ox molecules to replace those molecules which have spontaneously degraded to inactive $O_2$ and those which have reacted during the process.

Dynamic Ox biological burden reduction provides significant cost advantages over existing biological burden reduction technology. The most significant savings derive from the fact that the Ox biological burden reducing gas may be generated on site, during the process.

Because Ox is not flammable or explosive, facilities need not include damage-limiting construction or explosion-proof equipment. Another advantage of dynamic Ox biological burden reduction is that scrubbing will be easily accomplished using existing technology.

The dynamic Ox biological burden reduction process of the invention has proven successful in the treatment of mail and shipping parcels, while keeping the mail and shipping parcels intact.

Referring to FIG. 1, an apparatus that may be used to treat mail and shipping parcels at a mail processing facility in accordance with an embodiment of the method if the invention includes a biological burden reduction chamber 1 equipped with a gasketed door 2 that can be opened to accommodate placement of mail or shipping parcel 3 within the biological burden reduction chamber 1 and tightly closed and latched. The biological burden reduction chamber 1 permits a vacuum tight seal during the process. The chamber 1 is connected via piping 4 and appropriate control valves 5 to a vacuum pump 6 and separately to a generator of Ox 7, which, in turn is connected to a gas bubbler 8 and an air preparation regulated feed gas supply 9, which contains concentrated liquid $O_2$. The biological burden reduction chamber 1 is jacketed by coils of metal tubing (not shown) through which heated or chilled water generated by a temperature control (e.g., glycol) system (not shown) may be pumped to regulate the temperature within the chamber 1 during the biological burden reduction process. The entire biological burden reduction process may be controlled and monitored by a programmable industrial process controller 10. The bubbler 8 provides humidity control.

According to an embodiment of the invention, mail or shipping parcel 3 for which biological burden is to be reduced is placed within the biological burden reduction chamber 1 and the door 2 is closed and latched. The process is then initiated by activating the process controller 10, which has previously been programmed with the appropriate process parameters such as pressure, the specified temperature and humidity. The controller 10 first activates the vacuum pump 6 and ancillary valves 5a and 5b to reduce the biological burden reduction chamber pressure to a preset level between, e.g., 1 and 20 inches of mercury, and to maintain a desired temperature via the temperature control system. After the appropriate vacuum level has been reached, the controller 10 initiates biological burden reduction by activating the Ox generator 7 and opening a control valves 5a and 5b, allowing the washed Ox stream to be drawn into, through and out of the chamber 1 by the pressure differential. The vacuum pump 6 and Ox generator 7 operate continuously during the process.

Exposure to the Ox gas mixture may be varied in time, depending on the quantity of material being treated. Preferably, treatment is carried out for about 6 to 22 hours to achieve biological burden reduction. Once the biological burden reduction phase is complete, the vacuum pump 6 and Ox generator 7 are inactivated and fresh air is allowed to enter the chamber 1 via the air purge valve 5b. All Ox gases may then be passed through a commercially available catalytic destruct unit 9 which eliminates any residual $O_3$ and $O_1$ before the gas stream is discharged to the atmosphere. The treated material 3 can then be removed from the chamber 1 and is ready for delivery following appropriate tests to confirm biological burden reduction.

Figure 2:
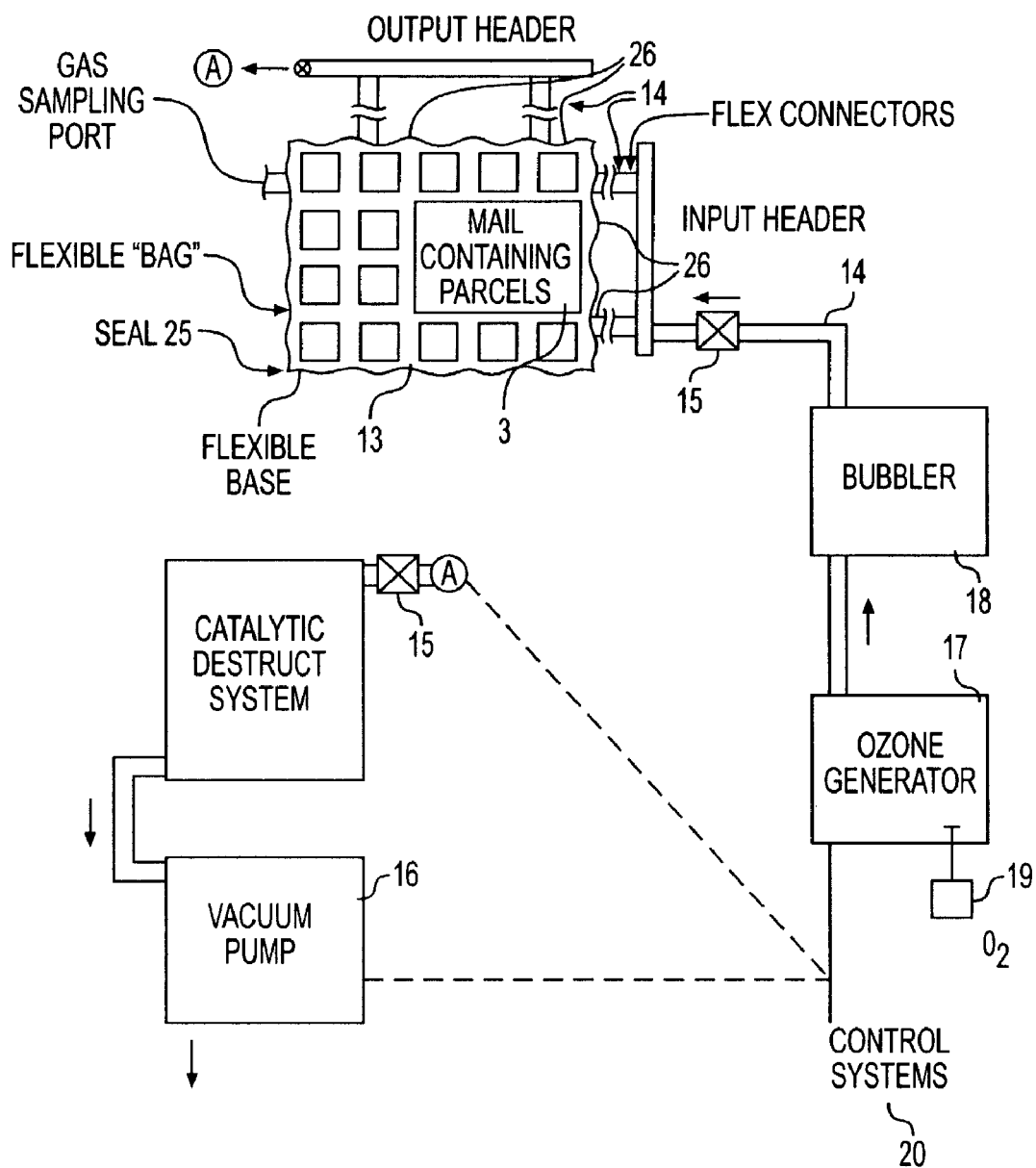
FIG. 2 is a schematic showing another example of an apparatus for using a continuous flow of $O_x$ to reduce biological burden or mail or shipping container in accordance with the method of the invention. Such an apparatus can be employed in the field.

Referring to FIG. 2, an apparatus that may be used to practice another embodiment of the method if the invention includes a flexible biological burden reduction chamber 13 that can be opened to accommodate placement of mail or shipping parcels 3 within the flexible biological burden reduction chamber 13 and tightly closed and sealed via a rapid closure system 25. The flexible biological burden reduction chamber 13 permits a vacuum tight seal during the process. The chamber 13 is connected via piping 14 and appropriate control valves 15 to a 15 vacuum pump 16 and separately to a generator of Ox 17, which, in turn is connected to a gas bubbler 18 and an air preparation regulated feed gas supply 19. A number of gas inlet and outlet ports 26 are configured so as to allow flowing gas to evenly penetrate the mail or shipping parcels. The entire biological burden reduction process may be controlled and monitored by a programmable industrial process controller 20.

According to another embodiment of the invention, mail or shipping parcel 3 for which biological burden is to be reduced is placed within the flexible biological burden reduction chamber 13 and the chamber is sealed closed. The process is then initiated by activating the process controller 20, which has previously been programmed with the appropriate process parameters such as pressure. The controller 20 first activates the vacuum pump 16 and ancillary valves 5 to reduce the flexible biological burden reduction chamber pressure to a preset level between, e.g., 1 and 20 inches of mercury. After the appropriate vacuum level has been reached, the controller 20 initiates biological burden reduction by activating the Ox generator 17 and opening a control valve 23, allowing the washed Ox stream to be drawn into, through and out of the flexible chamber 13 by the pressure differential. The vacuum pump 16 and Ox generator 17 operate continuously during the process.

Exposure to the Ox gas mixture may be varied in time from several minutes to several hours, depending on the material being treated. Once the biological burden reduction phase is complete, the vacuum pump 16 and Ox generator 17 are inactivated and fresh air is allowed to enter the flexible chamber 1 via the air purge valve 15. All Ox gases may then be passed through a commercially available catalytic destruct unit 24 which eliminates any residual $O_3$ and $O_1$ before the gas stream is discharged to the atmosphere. The treated material 3 can then be removed from the flexible chamber 13 and is ready for delivery following appropriate tests to confirm biological burden reduction.

Figure 3:
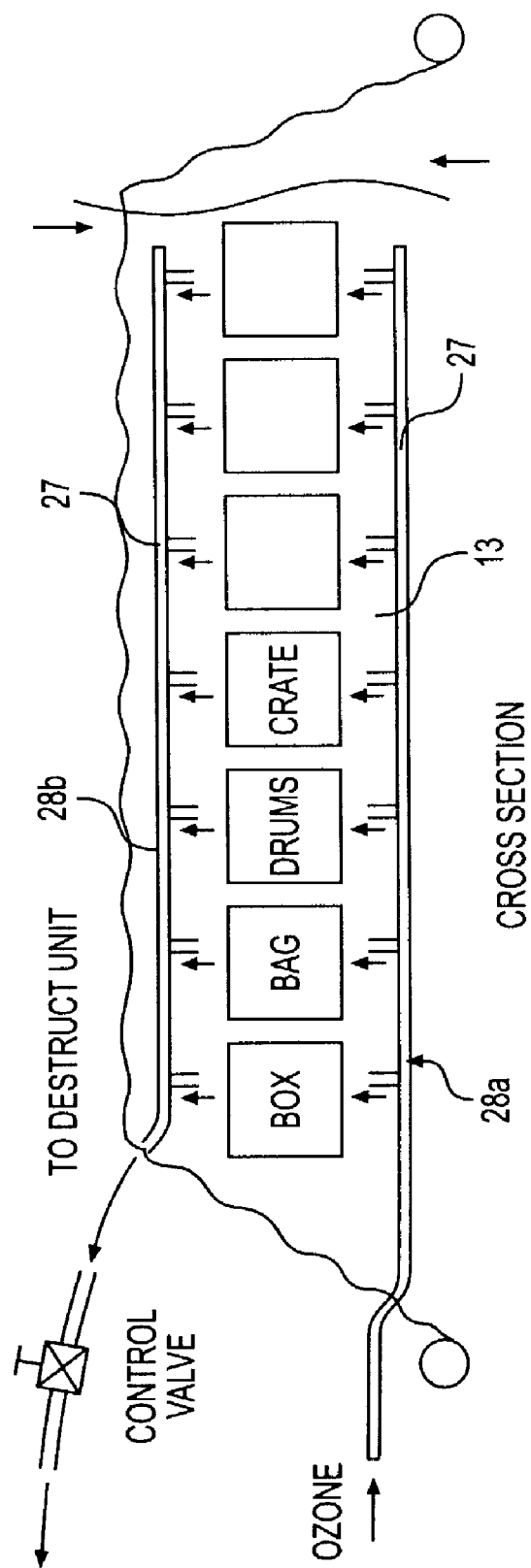
FIG. 3 is a schematic showing a header system that may be employed with the apparatus of FIG. 2.

Referring to FIG. 3, a header system 27 is employed. The header system 27, which includes collection header 28a and distribution header 28b, helps avoid gas streaming through the flexible biological burden reduction chamber 13.

EXAMPLES

The present invention will be further illustrated by the following non-limiting Examples.

Example 1

Tests performed using the apparatus and method of the invention were completed using biological indicator strips containing known quantities of *Bacillus subtilis* globigii spores, the accepted test organism for *Bacillus anthracis*.

Test strips containing $2 \times 10^6$ spores were placed in various types of sealed envelopes and parcels and treated in a biological burden reduction chamber for 8 hours using an ozone concentration of 4% and a relative humidity of 65% at 50° F. After treatment, the spore strips were incubated in a growth medium for 5 days and observed for growth. No growth occurred during this incubation period, thereby confirming the total destruction of the bacterial spores.

Example 2

Test strips containing $2 \times 10^6$ spores were placed in various types of sealed envelopes and parcels were treated in a flexible biological burden reduction chamber for 8 hours using an ozone concentration of 4% and a relative humidity of 65% at 68° F. After treatment, the spore strips were incubated in a growth medium for 5 days and observed for growth. No growth occurred during this incubation period, thereby confirming the total destruction of the bacterial spores.

The gaseous blend of Ox and method for applying the gaseous blend of Ox of the invention are thus an excellent substitute for prior treatments of mail components.

What is claimed:

1. A method for reducing biological burden on mail, comprising:
   (a) applying a continuous stream of Ox to said material in a sealed biological burden reduction chamber, wherein said Ox includes oxygen and its radicals; and
   (b) maintaining a predetermined pressure, temperature and relative humidity in said biological burden reduction chamber.

2. The method of claim 1, wherein said biological burden reduction chamber is constructed from an ozone resistant polymer.

3. The method of claim 2, further comprising conducting said biological burden reduction out in the field.

4. The method of claim 3, further comprising delivering said biological burden reduction chamber to an appropriate test facility to confirm an absence of biological burden.

5. The method of claim 2, wherein said biological burden reduction chamber further comprises two or more gas inlet ports and two or more gas outlet ports, wherein said two or more gas inlet ports and said two or more gas outlet ports permit said continuous flow of Ox to evenly penetrate said mail.

6. The method of claim 2, wherein said biological burden reduction chamber is maintained at ambient temperature.

7. The method of claim 2, wherein said biological burden reduction is conducted for a time of about 4 to about 20 hours.

8. The method of claim 7, wherein said biological burden reduction is conducted for a time of about 8 hours.

9. The method of claim 2, wherein said biological burden reduction is conducted using an ozone concentration of about 2% to about 8%.

10. The method of claim 2, wherein said biological burden reduction is conducted at a relative humidity below the dew point of ambient humidity.

11. The method of claim 2, wherein said biological burden reduction is conducted at a temperature of about 40° F. to about 100° F.

\* \* \* \* \*